US00PP36255P2

(12) United States Plant Patent
Dirr et al.

(10) Patent No.: US PP36,255 P2
(45) Date of Patent: Nov. 19, 2024

(54) ***BAPTISIA* PLANT NAMED 'PIIBAP-06-21'**

(50) Latin Name: ***Baptisia* hybrid**
Varietal Denomination: PIIBAP-06-21

(71) Applicant: Premier Introductions, Inc., Watkinsville, GA (US)

(72) Inventors: Michael Dirr, Bogart, GA (US); Jeff Beasley, Lavonia, GA (US); Mark Griffin, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/635,715

(22) Filed: Apr. 15, 2024

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Baptisia* plant named 'PIIBAP-06-21', characterised by rich indigo flowers that are held upright and contrast exquisitely with the yellowish green foliage. There are no other cultivated *Baptisia* exhibiting these characteristics known to the invention.

3 Drawing Sheets

Genus and species of plant claimed: *Baptisia* hybrid.
Variety denomination: 'PIIBAP-06-21'.

BACKGROUND OF THE INVENTION

The present invention relates to a new and distinct cultivar of hybrid *Baptisia*, hereinafter referred to by its cultivar name 'PIIBAP-06-21'. This cultivar is grown primarily as an herbaceous perennial for landscape and cut flowers. This cultivar originated from an open pollination of *Baptisia* x *variicolor* 'Twilite' (U.S. Plant Pat. No. 19,011) in Watkinsville, GA in 2019, and was selected from the progeny by continued evaluation for growth habit, floral, and foliage characteristics.

'PIIBAP-06-21' has been asexually reproduced by softwood cuttings since 2021 in Watkinsville, GA. The characteristics of the cultivar have been stable and reproduced true-to-type in successive vegetative generations.

SUMMARY OF THE INVENTION

'PIIBAP-06-21' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'PIIBAP-06-21' from all other varieties in commerce known to the Inventors. 1) Rich indigo flowers are held upright and contrast exquisitely with the yellowish green foliage. 2) Produces abundant flowers and stems with numerous flowers. 3) Strong stems holding inflorescence vertical. 4) Columnar shaped plant habit becoming more vase-shape as foliage develops.

PARENTAL COMPARISON

'PIIBAP-06-21' is distinguished from its parent plant *Baptisia* x *variicolor* 'Twilite' (U.S. Plant Pat. No. 19,011)

by leaf and leaflet color. 'PIIBAP-06-21' has yellowish green foliage, whereas 'Twilite' has green foliage. 'PIIBAP-06-21' has rich indigo flowers, but 'Twilite' has violet flowers.

COMMERCIAL COMPARISON

'PIIBAP-06-21' can be compared to the cultivar 'White Gold' (unpatented). 'White Gold' has chartreuse golden foliage with spikes of creamy white flowers. 'PIIBAP-06-21' has yellowish green foliage with rich indigo flowers. The flower spikes of 'PIIBAP-06-21' are longer than those on the cultivar 'White Gold'.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Baptisia*.

DETAILED DESCRIPTION

Figure 1:
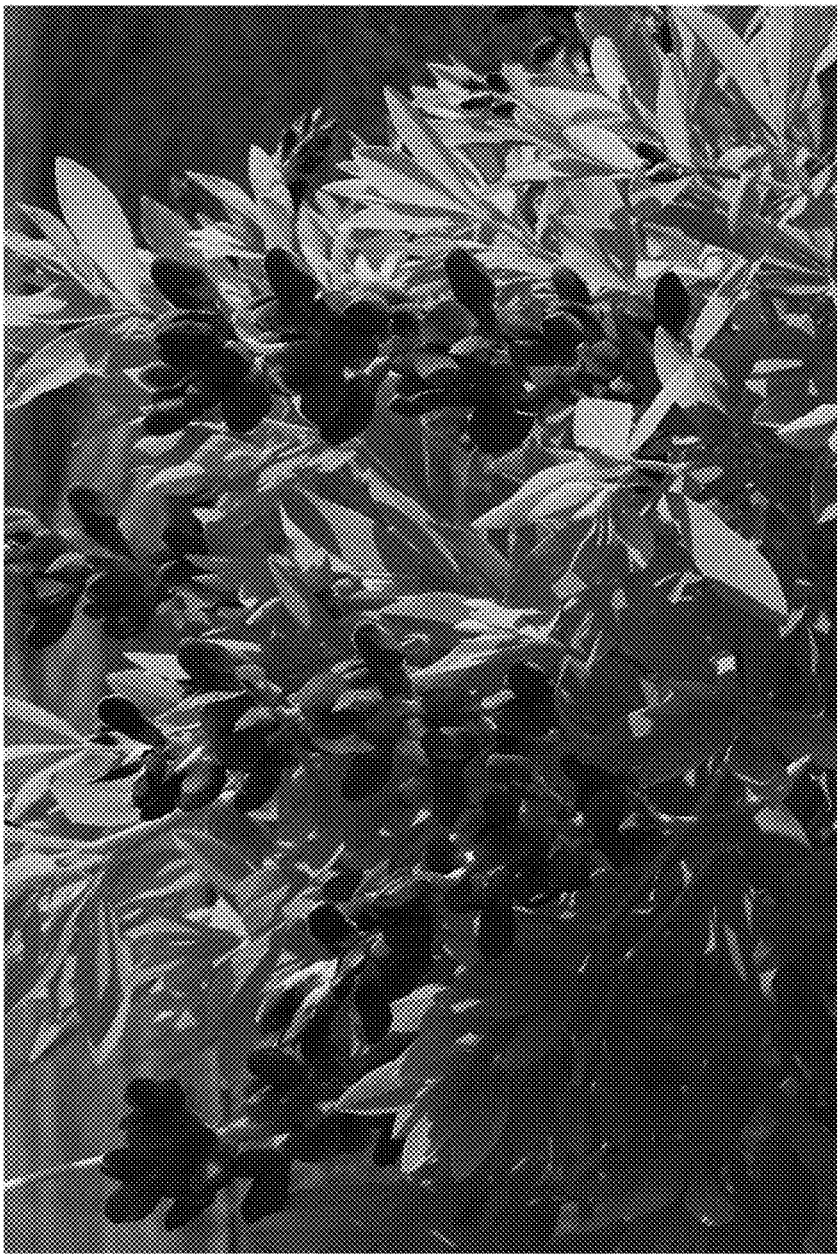
FIG. 1 shows a three-year-old 'PIIBAP-06-21' plant's rich indigo flowers with yellowish green foliage.
Figure 2:
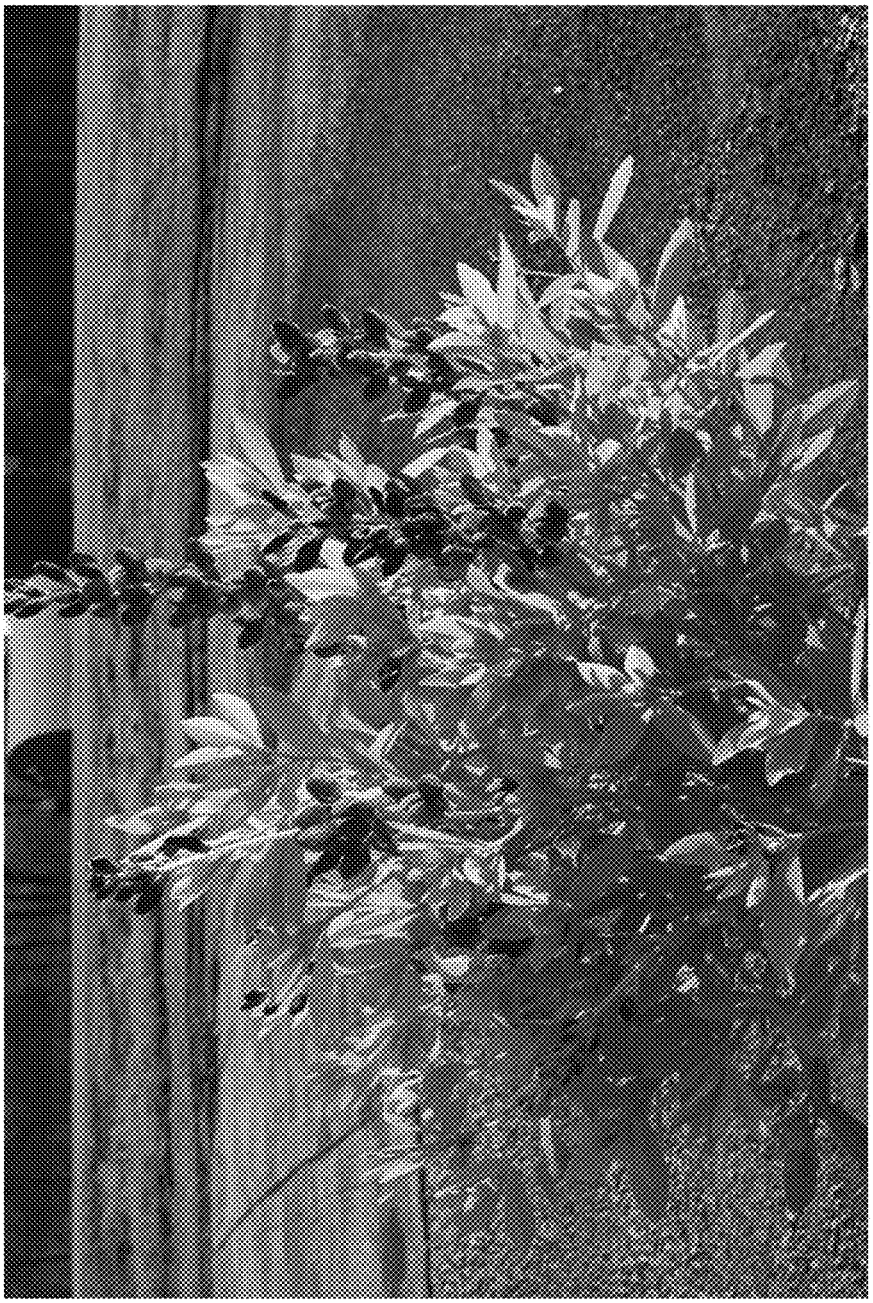
FIG. 2 shows a three-year-old 'PIIBAP-06-21' plant's yellowish green foliage.
Figure 3:
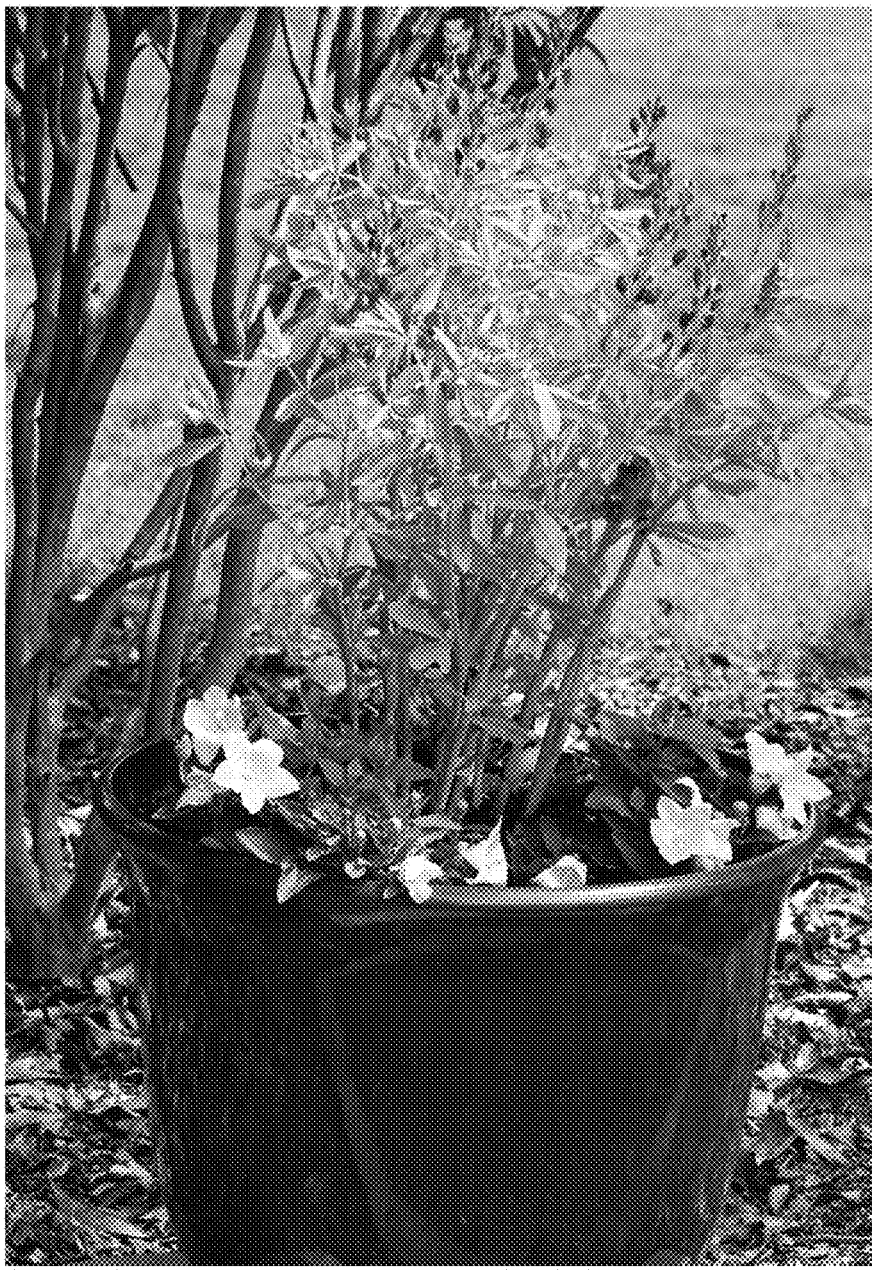
FIG. 3 shows a three-year-old 'PIIBAP-06-21' plant's habit.

In the following description, color references are made to The Royal Horticultural Society Colour Chart, 2015 Edition, except where general terms of ordinary dictionary significance are used. Plants for the description were grown in 11.35 L containers in greenhouse conditions in a nursery in Watkinsville, GA. Plants were about one year old when the description was recorded.

Botanical Classification: 'PIIBAP-06-21' is a cultivar of a hybrid *Baptisia*. The current variety is a progeny from an open pollination of *Baptisia* x *variicolor* 'Twilite' (U.S. Plant Pat. No. 19,011) in Watkinsville GA in 2019. Propagation: Vegetatively by stem cuttings taking about 3 weeks.

Plant description:

*Plant habit*.—Columnar shaped plant habit becoming more vase shape as foliage develops. The one-year-old plant in a container is 60 cm tall and 66 cm wide. Growth Rate: Fast, *Baptisia* emerge from the ground and are in flower in a month.

*Stem description*.—Branch habit: Densely branched; Primary branches 55° to 65° angle above horizontal; 13 branches with 3 secondary branches, and 2 tertiary branches. Stem size: 60 cm (including peduncle) in length and 7 mm in width; secondary: 21 cm in length and 3 mm in width; tertiary: 5 cm in length and 2 mm in width. Stem shape: Rounded. Stem color: 144C. Satiny, slightly glaucous. Internodes up to 5 cm apart, lowest branches internodes average about 7 cm.

*Roots*.—Deep rooted, thick, fleshy. Root Color: NN155A.

Leaves:

*Foliage*.—Fan shaped. Leaf division: Ternate. Leaf internode: Foliage begins 20 cm from the base, 7 cm on main stem and 5 cm on secondary branches. Leaf size: 7 cm in length and 8 cm in width when mature. Leaf quantity: about 23 per stem. Leaflet shape: Oblanceolate. Leaflet base: Cuneate. Leaflet apex: Acute. Foliage Venation: Pinnate pattern, not conspicuous, about 6-8 veins per leaflet; color matches leaflet color on upper and lower surface with mid rib of lower surface 146D. Leaflet margins: entire. Leaf attachment: Petiolate. Leaf arrangement: alternate. Leaflet surface: Glabrous and slightly glaucous on upper and lower surface. Leaflet color: Newly expanding foliage N144B on upper and lower surface; on mature leaflets N144A on upper and lower surface. Leaflet size 6 cm in length and 2 cm in width.

*Petioles*.—5 mm in length and 1.5 mm in width, clasping to stem at mature nodes, N144A in color, surface is glabrous and satiny. Stipules: lanceolate in shape, base is cuneate to stem, apex is narrowly acute to acuminate, 1 cm in length and 3 mm in width on mature leaves, 144B in color on upper and lower surface.

Flowers:

*Flower description*.—Inflorescence type: Terminal racemes of papilonaceous flowers on main and secondary branches, open from base to the apex, acropetal development. Inflorescence size: 21 cm in length and 4 cm in width in mid-section. Persistence of inflorescence: approximately 20 days. Flower size: 3 cm in length and 2 cm in diameter. Flower number per inflorescence about 30. Blooming Period: Six to eight weeks.

*Flower fragrance*.—None detected.

*Peduncle*.—Round in shape, 20 cm in length and 4 mm in width, 144A in color, surface is glabrous, satiny and slightly glaucous, flower internode length 3 cm to 4 cm. Pedicel: 5 mm in length and 1 mm in width, round in shape (cross section), 144A in color, glabrous and satiny surface. Flower buds: Kidney-shaped, 2 cm in length and 1 cm in width, 145A in color. Petal portion: 90C in color.

*Flower type*.—Papilionaceous, bilaterally symmetrical, held at a 45-degree angle. Calyx: Campanulate, about 1 cm in length and 6 mm in diameter, surface is glabrous and satiny, 145A. Sepals: 4 fused with exception of apex of each, free portion is triangular in shape 2.5 mm width and 2.5 mm in depth with acute apex, 145A in color. Corolla features: Papilionaceous (4 segments) with reflexed standard (banner), 2 lateral wings and a concealed keel. Standard (banner): orbicular and strongly reflexed in shape, 1.5 cm in length and 10 mm in width, upper and lower surfaces 90C with mid region having a base of 157A, apex rounded with a single notch, surface is glabrous on all sections. Lateral wings: lanceolate in shape 2 cm in height and 10 mm in width, upper surface and lower surface 90B with base of NN155C, rounded apex and oblique base. Keel: not visible, comprised of 2 segments surrounding reproductive organs, lanceolate in shape with rounded apex and oblique base, 1.5 cm in length and 10 mm in width, upper and lower surfaces are NN155A in color, segments joined at center point.

*Receptacle*.—Disk shaped, gelatinous, 144A in color, 3 mm in diameter and 1 mm in depth. Reproductive organs: Gynoecium: 1 pistil 1.7 cm in length, 1 mm in depth; style is 145B in color and 5 mm in length; stigma less than.5 mm 150B in color.

*Ovary*.—Superior above hypanthium, suspended by style; 6 mm long and 1.5 mm in diameter; color 145B. Style 4 mm long, and 0.5 mm diameter color 145B. Androecium: Stamens ten. Filament: Glabrous; slightly lustrous; not united 2 cm in length, less than 1 mm diameter, slightly curved upward distally; color 150D. Anther: dorsifixed, oblong 1.5 mm long and 1 mm wide; color 15A. Pollen: Spherical; abundant; color 15A.

Fruit:

*Fruit*.—Bivalve inflated ellipsoidal pod; glabrous, 5 cm long and 4 cm across and about 2 mm thick, color starting at N144A and maturing to 200A, numerous seeds per pod (open pollinated), reniform, glabrous, about 4 mm long, 3 mm across, and 2 mm thick, color N199B.

Plant hardiness:

*Plant hardiness*.—USDA Hardiness Zone Map (2012): Zones 4a-9b; heavy clay or light loamy sand soils; able to withstand drought conditions once established.

Disease/pest resistance: Susceptibility or resistance to diseases beyond that typically found in other false indigo plants has not been observed.

We claim:

1. A new and distinct *Baptisia* plant named 'PIIBAP-06-21', substantially as illustrated and described herein.

* * * * *